(12) United States Patent  
Kline et al.

(10) Patent No.: US 7,980,148 B2  
(45) Date of Patent: Jul. 19, 2011

(54) DEVICE FOR SAMPLING PLANT MATERIAL

(75) Inventors: Daniel S. Kline, Encinitas, CA (US); Anthony David Barghini, Encinitas, CA (US); Scott Wayne Beaver, San Marcos, CA (US); James Coleman Lee, San Diego, CA (US); William Michael Lafferty, Encinitas, CA (US)

(73) Assignee: Syngenta Participations AG, Basel (CH)

( * ) Notice: Subject to any disclaimer, the term of this patent is extended or adjusted under 35 U.S.C. 154(b) by 525 days.

(21) Appl. No.: 11/948,491

(22) Filed: Nov. 30, 2007

(65) Prior Publication Data

US 2009/0139353 A1 Jun. 4, 2009

(51) Int. Cl.  
*G01N 1/04* (2006.01)

(52) U.S. Cl. ..................................... 73/864.45

(58) Field of Classification Search ............... 73/864.41, 73/864.44, 864.45  
See application file for complete search history.

(56) References Cited

U.S. PATENT DOCUMENTS

| 3,921,459 | A | * | 11/1975 | Willett | 73/864.41 |
| 5,190,666 | A |   | 3/1993  | Bisconte | 210/744 |
| 6,103,518 | A |   | 8/2000  | Leighton | |
| 6,959,617 | B2 |  | 11/2005 | Depperman | |
| 7,134,351 | B2 |  | 11/2006 | Depperman | |
| 7,454,989 | B2 |  | 11/2008 | Depperman | |
| 2002/0164272 | A1 | | 11/2002 | Harris | 422/101 |
| 2005/0066751 | A1 | * | 3/2005 | Harris | 73/864.45 |
| 2005/0228310 | A1 |   | 10/2005 | Pfistershammer | 600/567 |
| 2006/0121596 | A1 | * | 6/2006 | Chaumat | 435/283.1 |
| 2007/0093728 | A1 |   | 4/2007 | Douglas et al. | 600/583 |
| 2008/0227662 | A1 | * | 9/2008 | Stromberg et al. | 506/39 |
| 2009/0042180 | A1 | * | 2/2009 | Lafferty et al. | 435/4 |

FOREIGN PATENT DOCUMENTS

GB 2414700 A * 12/2005

* cited by examiner

*Primary Examiner* — Hezron Williams  
*Assistant Examiner* — Tamiko D Bellamy  
(74) *Attorney, Agent, or Firm* — Dana Rewoldt

(57) ABSTRACT

A device for collecting plant samples includes a punch and die mechanism for taking leaf plugs from plants. The punch itself includes a punch rod coaxially mounted inside a punch tube. In use, the punch tube has a distal end with two, diametrically opposed projections that interact with the formed aperture to cut a plug from a plant leaf. The punch rod then follows to remove a cut leaf plug from the formed aperture. Also included is a hydraulic subsystem for periodically delivering liquid on the punch and die mechanism to prevent plant debris from clogging the device.

20 Claims, 3 Drawing Sheets

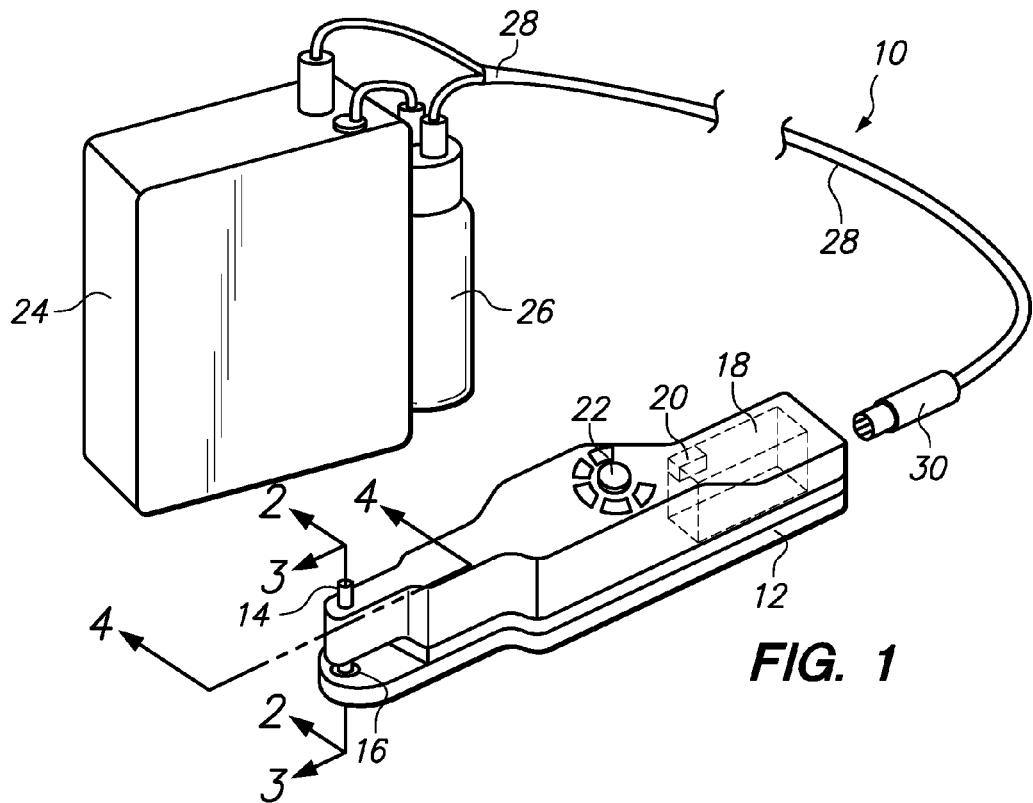
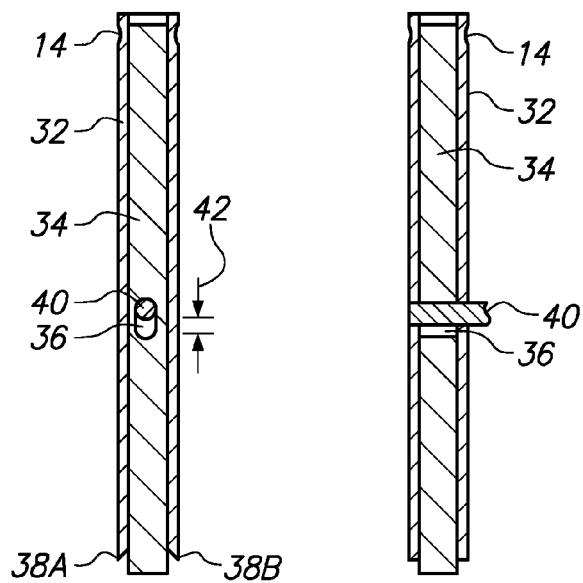

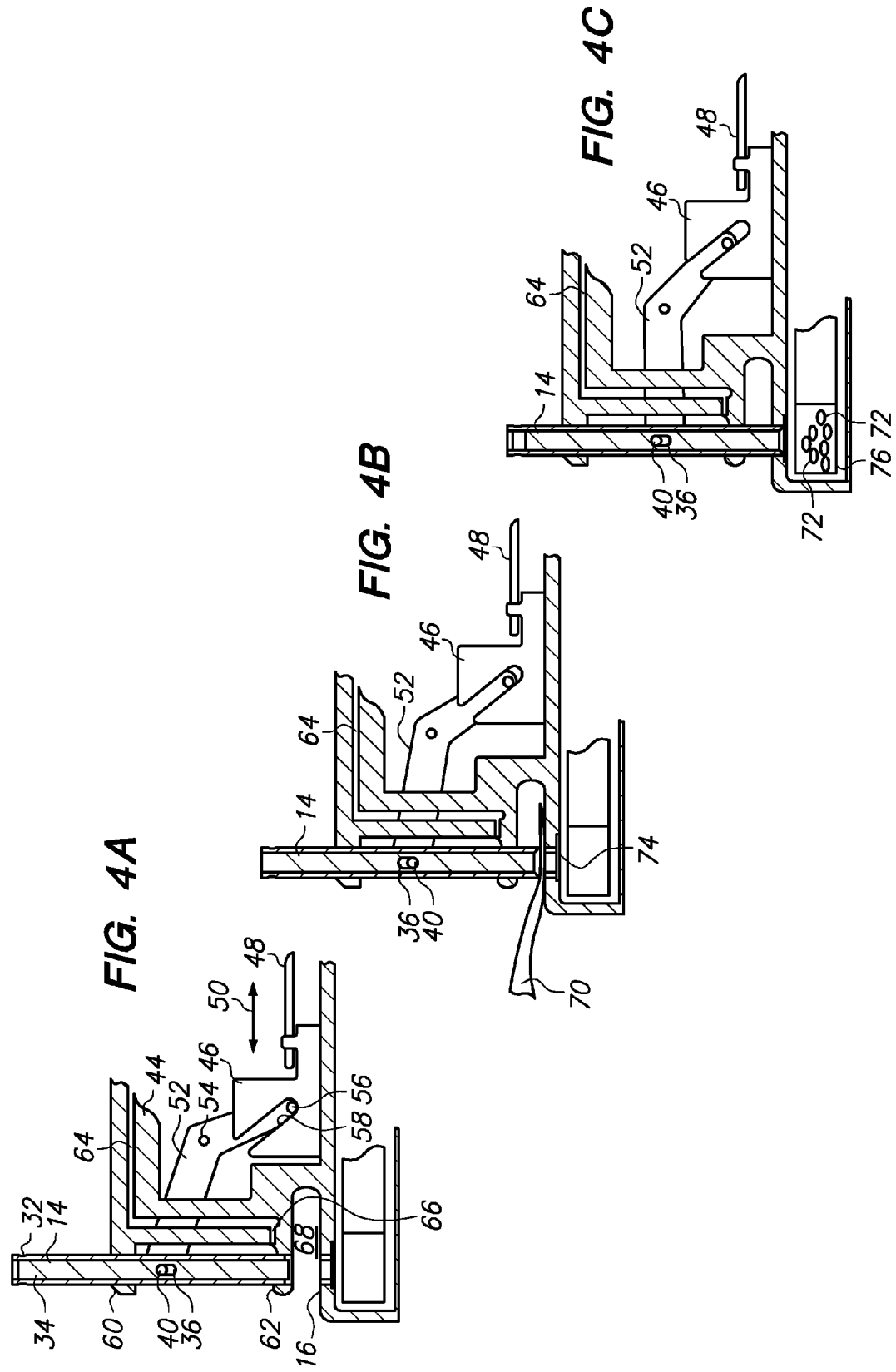

DEVICE FOR SAMPLING PLANT MATERIAL

FIELD OF THE INVENTION

The present invention pertains generally to sampling systems. More particularly, the present invention pertains to systems that provide for marker assisted breeding and the quality control of agricultural plants. The present invention is particularly, but not exclusively useful for obtaining genetic markers from a vast number of plants that will help select plants with a desired genotype and/or phenotype.

BACKGROUND OF THE INVENTION

It is well known that genetic markers can be obtained from DNA and used for a variety of purposes. For example, in the field of agriculture, the DNA that is taken from plant material will yield genetic markers that can be used in marker assisted breeding. In this process, DNA sequences are used to follow desirable agronomic traits in the process of plant breeding.

For marker assisted breeding, seeds of plants with a desired trait are planted either in a greenhouse, in a field or in a hydroponic system. Plant tissue (for example, leaf) is then harvested from the plants for preparation of DNA once sufficient tissue can be removed from the plants without compromising their viability. Thus, genomic DNA is isolated for further processing to find specific genetic characteristics. In the subsequent processing, these characteristics are linked to traits of interest and are thereby used to predict the presence or absence of the traits of interest in the sampled plants.

As a practical matter, the identification of plants involves complicated procedures that are difficult, if not impossible, to accomplish on-site in the field. The situation becomes further complicated when a large number of plants are involved, such as in a commercial agricultural operation where thousands, or tens of thousands, of different plants are being cultivated in the same field. In such operations, the ability to subsequently identify a particular plant may be of crucial importance. Further, the samples must be easily collected and efficiently presented for processing. Also, whatever device is used to collect the samples of plant material must be capable of reliable operation through many repetitive cycles, for prolonged periods of time. For instance, samples may need to be taken from several thousand different plants. According to the present invention, these samples can be taken from different plant tissue, including but not limited to stem, root, or seed tissue. Preferably, these samples can be taken from the leaves or cotyledons of the plants.

A particularly effective mechanism for collecting samples of plant material is the rather well known punch and die. Such a mechanism, however, is not problem-free. For one, the punch and die must consistently remove samples from the plants without fouling the mechanism. This requires a clean cut of the sample, and an effective separation of the cut sample from the plant. For another, any clogging or contamination of the punch mechanism that might result from the accumulation of solid and liquid debris must be avoided or, at least, minimized. On this last point, it has been determined that the punch clogging phenomenon is highly dependent on the ambient temperature and the relative humidity. Within these parameters, a warm, dry ambient condition has been determined to be most conducive to punch clogging. Tests have shown, however, that this problem can be effectively alleviated by periodically applying water on the punch and die mechanism.

In light of the above, it is an object of the present invention to provide a device for collecting samples of material from plants that consistently cuts and removes samples from a plant for further processing. Another object of the present invention is to achieve sustained operation of a device for collecting samples of material from plants by effectively preventing any clogging of the device by solid and liquid debris. Still another object of the present invention is to provide a device for collecting samples of material from plants that is easy to use, is relatively simple to manufacture, and is comparatively cost effective.

SUMMARY OF THE INVENTION

A device for collecting samples of material from plants includes a punch and die mechanism that is mounted on a base member. The punch portion of this mechanism includes a punch tube in combination with a punch rod. In detail, the punch tube is elongated and cylindrical shaped. It also has a distal end that is formed with two cutting projections. Specifically, the cutting projections extend axially in a distal direction from the distal end of the punch tube. In combination, the punch rod is coaxially positioned for reciprocal movement inside the lumen of the punch tube. The formed aperture portion of the mechanism is annular shaped and is mounted on the base member to interact with the punch portion.

In their combination, the punch tube and the punch rod require a link rod that holds them in predetermined relationships. For this purpose, the wall of the punch tube is formed with a pair of diametrically opposed holes. On the other hand, the punch rod is formed with a single, axially oriented, oblong hole. The link rod is then inserted through the pair of axially opposed holes in the punch tube, and also through the oblong hole of the punch rod. Thus, axial movements of the punch rod in the lumen of the punch tube are limited by the length of its oblong hole. More specifically, within the lumen of the punch tube, the punch rod can move between a first position and a second position. In the first position, the distal end of the punch rod is proximal to the distal end of the punch tube. In the second position, the distal end of the punch rod is distal to the distal end of the punch tube.

As intended for the present invention, movements of the punch tube and punch rod are initiated by a drive mechanism. Structurally, this drive mechanism is mounted on the base member and involves the interaction of an actuator, a drive rod, a cam block and a yoke. In detail, the cam block is relatively compact in structure and is mounted for reciprocal movement on the base member. It is formed with a slot. The yoke, on the other hand, is an elongated member having a first end and a second end with a midpoint therebetween. The yoke also includes a pin that is affixed to its second end. With this structure, the yoke is pivotally mounted on the base member at its midpoint. In this arrangement, the first end of the yoke is engaged with the link rod that holds the punch rod in the lumen of the punch tube, and the pin at the second end of the yoke is positioned in the slot of the cam block.

In an operation of the device of the present invention, the actuator moves the drive rod. In turn, the drive rod moves the cam block. As the cam block moves, the pin on the yoke is guided along the slot in the cam block to rotate the yoke. With a rotation of the yoke, the yoke urges against the link rod and this causes the punch tube and punch rod combination to move relative to the formed aperture. More specifically, the punch tube is moved between first and second locations. During this movement of the punch tube, the punch rod moves back and forth between distal and proximal positions in the lumen of the punch tube. In its first (retracted) location, the distal end of the punch tube is at a distance from the formed aperture to create a gap between them for receiving a leaf therein. Also, the punch rod is at its distal position in the lumen of the punch tube. In its second location, the distal end of the punch tube is in contact with the formed aperture. As the punch tube moves between these locations, the projections on the distal end of the punch tube interact with the formed aperture to cut a leaf plug from the leaf in the gap. Also, due to its inertia, the punch rod is at its proximal position in the lumen of the punch tube during this movement of the punch tube. After the leaf plug has been cut (i.e. the punch tube is in its second location), the punch tube stops while the movement of the punch rod continues. Specifically, the momentum of the punch rod initiates a movement of the punch rod relative to the punch tube, causing the punch rod to move from its proximal position to its distal position. This movement of the punch rod then removes the cut leaf plug from the formed aperture for its collection.

An additional feature of the device of the present invention is an apparatus for irrigating the punch and die mechanism. Specifically, this irrigating apparatus includes a source of water (or a solvent, e.g. alcohol) and a transfer tube. The transfer tube has a first end that is connected in fluid communication with the water source, and it has a second end that is positioned to selectively deliver pressurized water onto the respective distal ends of the punch tube and punch rod, as well as onto the formed aperture. Further, this selective delivering can be periodically accomplished, as desired (e.g. after every 50 leaf plug cuts). The purpose here is to prevent clogging of the device with leaf debris.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of the device of the present invention;

FIG. 2 is a cross section view of the punch mechanism of the device as seen along the line 2-2 in FIG. 1;

FIG. 3 is a cross section view of the punch mechanism of the device as seen along the line 3-3 in FIG. 1;

FIG. 4A is a cross section view of the punch activation mechanism of the device as seen along the line 4-4 in FIG. 1, at the beginning of a punch cycle;

FIG. 4B is a cross section view of the punch activation mechanism of the device as seen along the line 4-4 in FIG. 1, during a punch cycle;

FIG. 4C is a cross section view of the punch activation mechanism of the device as seen along the line 4-4 in FIG. 1, at the end of a punch cycle;

DESCRIPTION OF THE PREFERRED EMBODIMENTS

Figure 5A:
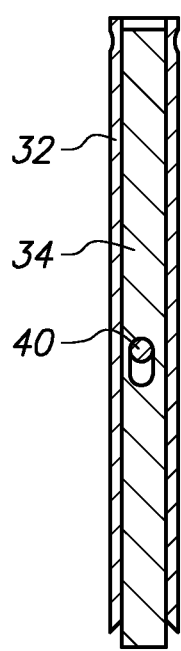
FIG. 5A corresponds to FIG. 4A and is an enlarged view showing the punch rod in its distal position.

Referring initially to FIG. 1, a device for collecting samples of plant material in accordance with the present invention is shown and is generally designated 10. As shown, in one embodiment of the invention the device 10 includes a leaf sampler 12 that has a punch mechanism 14, and a formed aperture 16 at its forward end. Shown in phantom in FIG. 1 is an actuator 18 that is mounted inside the leaf sampler 12. Also shown in phantom is a valve 20 that is mounted with the actuator 18 inside leaf sampler 12. FIG. 1 further shows that the leaf sampler 12 includes a keypad 22 that can be manipulated by a user (not shown) to operate the actuator 18 and the valve 20 of the leaf sampler 12.

Still referring to FIG. 1, it will be further seen that the device 10 includes a power pack 24 and a source 26 of pressurized liquid. Both of these components, the power pack 24 and the liquid source 26, are operatively connected to the leaf sampler 12 via a cable 28 and a connector 30. As intended for the present invention, these connections allow a user to independently and separately accomplish two separate tasks for the leaf sampler 12. For one, power from the power pack 24 can be used to activate the actuator 18 that, in turn, moves the punch mechanism 14 of the leaf sampler 12. For another, pressurized liquid from the liquid source 26 can be provided for cleaning the punch mechanism 14. These tasks can be accomplished simply by manipulation of the keypad 22.

Turning now to FIGS. 2 and 3, the punch mechanism 14 is shown to include a punch tube 32 in combination with a punch rod 34. In this combination, the punch tube 32 is an elongated hollow tube that is formed with a lumen. On the other hand, the punch rod 34 is substantially solid and is disposed in the lumen of the punch tube 32 for back and forth axial movements along the length of the punch tube 32. Further, as shown in both FIG. 2 and FIG. 3, the punch rod 34 is formed with an oblong hole 36 that is located approximately midway between the ends of the punch rod 34. Also, the distal (lower) end of the punch tube 32 is formed with a pair of diametrically opposed projections 38a and 38b (see FIG. 2). For purposes of the present invention, the projections 38a and 38b are formed using a cylindrical drill (cutter) to engage the punch tube 32 at a right angle to its longitudinal axis.

As shown in FIGS. 2 and 3, the punch rod 34 is supported in the lumen of punch tube 32 by a link rod 40. This link rod 40 is rigidly affixed to the punch tube 32 and extends diametrically across its lumen. The link rod 40 also passes through the oblong hole 36 in the punch rod 34. With this structural combination, limited axial movements of the punch rod 34 in the lumen of punch tube 32 are made possible by the interaction of oblong hole 36 in the punch rod 34 with the link rod 40. Specifically, these limited movements of punch rod 34 relative to punch tube 32 are confined to the distance 42 shown in FIG. 2.

FIG. 4A indicates the leaf sampler 12 includes a base member 44 on which the punch mechanism 14 and the formed aperture 16 are mounted. Also, a cam block 46 is mounted on the base member 44 and is attached to a drive rod 48. In turn, the drive rod 48 is connected to the actuator 18 (see FIG. 1). With this connection, the actuator 18 is able to move the cam block 46 back and forth on the base member 44 in the direction of arrows 50. FIG. 4A also indicates that a yoke 52 is mounted on the base member 44 for rotation about a pivot point 54. Further, as shown, a pin 56 is affixed to one end of the yoke 52 and it (the pin 56) is positioned in a slot 58 that is formed on the cam block 46. The end of yoke 52 that is opposite from the pin 56 is attached directly to the link rod 40 and indirectly to the punch tube 32 of punch mechanism 14 via link rod 40.

Still referring to FIG. 4A, it is seen that the punch mechanism 14 is held in position on the base member 44 by an upper guide 60 and a lower guide 62. Together, the guides 60 and 62 require the punch mechanism 14 travel on a linear path toward, and away from, the formed aperture 16. FIG. 4A also shows that the base member 44 is formed with a fluid pathway 64 that interconnects a nozzle 66 in fluid communication with the valve 20 (see FIG. 1). With this connection, a fluid pathway 64 is established between the pressurized liquid source 26 and the nozzle 66 that can be effectively controlled by operation of the valve 20. FIG. 4A further shows that the base member 44 is shaped to establish a gap 68 that is located on the base member 44 between the punch mechanism 14 and the formed aperture 16.

Operation

Figure 5B:
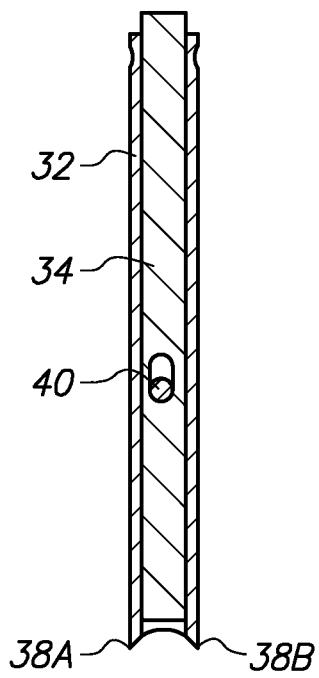
FIG. 5B corresponds to FIG. 4B and is an enlarged view showing the punch rod in its proximal position.
Figure 5C:
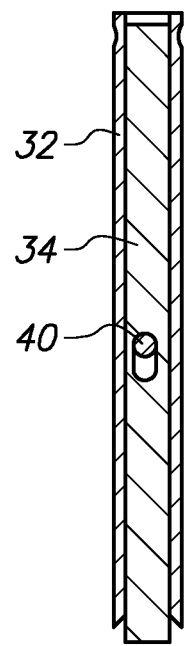
FIG. 5C corresponds to FIG. 4C and is an enlarged view showing the punch rod in its distal position.

The operation of the device 10 of the present invention will be best appreciated with collective reference to FIGS. 4A, 4B and 4C and with respective reference to FIGS. 5A, 5B and 5C. With this collective reference, an operational cycle of the device 10 begins with the leaf sampler 12 configured as shown in FIG. 4A (see also FIG. 5A). A leaf 70 (see FIG. 4B) can then be inserted into the gap 68. With a leaf 70 so positioned in the gap 68, the user (not shown) manipulates the keypad 22 to activate the actuator 18. This causes the actuator 18 to move the drive rod 48, and to thereby move the cam block 46 sequentially through the positions shown respectively in FIGS. 4A, 4B and 4C. Consequently, the yoke 52 and punch mechanism 14 are also sequentially moved through the positions shown respectively in FIGS. 4A, 4B and 4C (see also FIGS. 5A, 5B and 5C).

An aspect of the present invention can be appreciated by comparing the relative positions of the punch tube 32 and punch rod 34 as they move through the configurations shown in FIGS. 4A, 4B and 4C (see also corresponding FIGS. 5A, 5B and 5C). First compare FIG. 4A with FIG. 4B. In the cycle start position (FIG. 4A), the punch rod 34 effectively hangs at a distal position in the lumen of punch tube 32 from the link rod 40 (FIG. 5A). With the activation of an operational cycle, however, the cam block 46 and yoke 52 combine to mechanically drive the link rod 40 in a direction toward the formed aperture 16 (see FIG. 4B). Recall, the link rod 40 is connected directly to the punch tube 32. The link rod 40, however, is also located in the oblong hole 36 in punch rod 34. Thus, due to a consequent rapid acceleration to the link rod 40, the link rod 40 effectively drives both the punch tube 32 and the punch rod 34 toward the formed aperture 16. The inertia of punch rod 34, however, causes it to move to a proximal position in the lumen of punch tube 32 (see the location of link rod 40 in oblong hole 36 of the punch rod 34 in FIGS. 4B and 5B). During this movement, the exposed projections 38a and 38b on the punch tube 32 cut a leaf plug 72 from the leaf 70.

Now consider FIG. 4B with FIG. 4C. As shown in FIG. 4B, while the punch tube 32 is cutting a leaf plug 72 from leaf 70, the punch rod 34 is withdrawn to its proximal position in the lumen of the punch tube 32 (see FIG. 5B). As implied above, this withdrawal of punch rod 34 into the lumen of punch tube 32 results from the inertia of punch rod 34. When the punch tube 32 contacts the abutment 74 below formed aperture 16, however, this changes. Specifically, as best appreciated with reference to FIG. 4C, although the abutment 74 stops the punch tube 32, it does not stop the punch rod 34 at the same time. Instead, due to its momentum, the punch rod 34 continues to move through the distance 42 (FIG. 2) and return to its distal position (see FIG. 5C). This additional movement effectively clears the leaf plug 72 from formed aperture 16 and deposits the leaf plug 72 into the sample container 76 for further processing. As a final step in an operational cycle of the leaf sampler 12, it returns to the configuration shown in FIG. 4A.

In the illustrated embodiment, inertia and momentum are used to provide the movement of the punch rod 34 relative to the punch tube 32. Alternatively, movement of the punch rod 34 relative to the punch tube 32 could be mechanically actuated.

As intended for the present invention, the punch mechanism 14 needs to be irrigated to remove solid and liquid leaf debris. Specifically, the punch mechanism 14 may become clogged by leaf debris that wedges between the punch rod 34 and the aperture 16. Also, leaf debris may adhere to the punch mechanism 14 and be carried by the punch mechanism 14 up from the gap 68 and into the base member 44. In either case, the leaf debris may be removed by manipulating the keypad 22. Thus, whenever an appropriate entry is made on keypad 22, the valve 20 releases liquid from the pressurized liquid source 26. This liquid then progresses through the pathway 64, and through the nozzle 66, onto the punch mechanism 14. Alternatively, this irrigation can be accomplished periodically, at timed intervals, or constantly. However applied, the liquid irrigates the punch mechanism 14 in the vicinity of the projections 38a and 38b to remove solid and liquid leaf debris that would otherwise clog the punch mechanism 14. Preferably, the punch mechanism 14 is irrigated after approximately fifty leaf plugs 72 have been collected. In certain embodiments, the liquid may be water or solvent. Alternatively, the liquid may include anti-biotic, anti-viral, or anti-pathogenic compounds to reduce cross contamination by the punch mechanism 14.

While the particular Device for Sampling Plant Material as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for collecting samples of material from plants which comprises:
    a base member;
    a formed aperture mounted on the base member;
    a punch tube formed with a hollow lumen and having a proximal end and a distal end, the punch tube being mounted on the base member for movement between a first location wherein the distal end of the punch tube is at a distance from the formed aperture to establish a gap therebetween for receiving a plant specimen therein, and a second location wherein the distal end of the punch tube is in contact with the formed aperture to cut a plug from the plant specimen;
    a punch rod having a proximal end and a distal end, the punch rod being coaxially mounted in the lumen of the punch tube for movement therein between a first position wherein the distal end of the punch rod is proximal to the distal end of the punch tube and a second position wherein the distal end of the punch rod is distal to the distal end of the punch tube; and
    a drive mechanism for selectively moving the punch tube from its first location to its second location, wherein said punch tube cuts a plug from the plant specimen, and for initiating a subsequent movement of the punch rod from its first position to its second position to remove the cut plant specimen plug from the formed aperture for collection thereof.

2. A device as recited in claim 1 wherein the distal end of the punch tube is formed with a pair of diametrically opposed projections.

3. A device as recited in claim 1 wherein the punch tube defines an axis and is formed with a pair of diametrically opposed holes, wherein the punch rod is formed with an axially oriented oblong hole, and further wherein the device comprises a link rod inserted through the pair of axially opposed holes in the punch tube and through the oblong hole of the punch rod to mount the punch rod and the punch tube, in combination, on the base member.

4. A device as recited in claim 3 wherein the drive mechanism comprises:
   a drive rod;
   a cam block formed with a slot and mounted on the base member for engagement with the drive rod;
   a yoke having a first end and a second end with a midpoint therebetween, the yoke being pivotally mounted on the base member at its midpoint and having its first end engaged with the link rod;
   a pin affixed at the second end of the yoke and positioned in the slot of the cam block; and
   an actuator mounted on the base member and connected to the drive rod for moving the drive rod, to simultaneously pivot the yoke and drive the punch tube between its first location and second location.

5. A device as recited in claim 1 wherein the formed aperture includes a hardened steel insert.

6. A device as recited in claim 1 further comprising:
   a source of liquid;
   a transfer tube having a first end and a second end, wherein the first end is connected in fluid communication with the source of liquid and the second end is positioned to selectively deliver liquid therefrom onto the respective distal ends of the punch tube and the punch rod, and onto the formed aperture, to prevent clogging of the device with solid and liquid plant debris; and
   a means for transferring liquid through the transfer tube.

7. A device as recited in claim 6 wherein the liquid transferring means comprises:
   a means for pressurizing the source of liquid; and
   a control valve mounted on the base member to selectively deliver pressurized liquid from the transfer tube.

8. A device as recited in claim 7 wherein the control valve is automatically activated after a set of approximately fifty (50) plugs have been cut.

9. A device for collecting samples of material from plants which comprises:
   a base member;
   a mechanical means mounted on the base member for cutting a plug from a plant specimen;
   an electronic means mounted on the base member for selectively activating the cutting means; and
   a hydraulic means mounted on the base member for irrigating the cutting means to prevent clogging of the device with solid and liquid plant debris.

10. A device as recited in claim 9 wherein the cutting means comprises:
    a formed aperture mounted on the base member;
    a punch tube formed with a hollow lumen and having a proximal end and a distal end, the punch tube being mounted on the base member for movement between a first location wherein the distal end of the punch tube is at a distance from the formed aperture to establish a gap therebetween for receiving the plant specimen therein, and a second location wherein the distal end of the punch tube is in contact with the a formed aperture to cut a plug from the plant specimen; and
    a punch rod having a proximal end and a distal end, the punch rod being coaxially mounted in the lumen of the punch tube for movement therein between a first position wherein the distal end of the punch rod is proximal to the distal end of the punch tube and a second position wherein the distal end of the punch rod is distal to the distal end of the punch tube.

11. A device as recited in claim 10 wherein the cutting means further comprises a drive mechanism for selectively moving the punch tube from its first location to its second location to cut a plug from the plant specimen, and for initiating a subsequent movement of the punch rod from its first position to its second position to remove the cut plant specimen plug from the formed aperture for collection thereof.

12. A device as recited in claim 10 wherein the distal end of the punch tube is formed with a pair of diametrically opposed projections.

13. A device as recited in claim 10 wherein the punch tube defines an axis and is formed with a pair of diametrically opposed holes, wherein the punch rod is formed with an axially oriented oblong hole, and further wherein the device comprises a link rod inserted through the pair of axially opposed holes in the punch tube and through the oblong hole of the punch rod to mount the punch rod and the punch tube, in combination, on the base member.

14. A device as recited in claim 13 wherein the drive mechanism comprises:
    a drive rod;
    a cam block formed with a slot and mounted on the base member for engagement with the drive rod;
    a yoke having a first end and a second end with a midpoint therebetween, the yoke being pivotally mounted on the base member at its midpoint and having its first end engaged with the link rod; and
    a pin affixed at the second end of the yoke and positioned in the slot of the cam block, wherein the actuator is connected to the drive rod for moving the drive rod, to simultaneously pivot the yoke and drive the punch tube between its first location and second location.

15. A device as recited in claim 9 wherein the hydraulic means comprises:
    a source of liquid;
    a transfer tube having a first end and a second end, wherein the first end is connected in fluid communication with the source of liquid and the second end is positioned to selectively deliver liquid therefrom onto the respective distal ends of the punch tube and the punch rod, and onto the formed aperture, to prevent clogging of the device with solid and liquid plant debris; and
    a means for transferring liquid through the transfer tube.

16. A device as recited in claim 15 wherein the liquid transferring means comprises:
    a means for pressurizing the source of liquid; and
    a control valve mounted on the base member, the control valve being automatically activated to selectively deliver pressurized liquid from the transfer tube after a set of approximately fifty (50) plugs have been cut.

17. A method for using a device to collect samples of material from plants wherein the device comprises a base member, an annular shaped formed aperture mounted on the base member, a punch tube formed with a hollow lumen and having a proximal end and a distal end; the punch tube being mounted on the base member for movement between a first location wherein the distal end of the punch tube is at a distance from the formed aperture to establish a gap therebetween for receiving a plant specimen therein, and a second location wherein the distal end of the punch tube is in contact with the formed aperture to cut a plug from the plant specimen, and a punch rod having a proximal end and a distal end, the punch rod being coaxially mounted in the lumen of the punch tube for movement therein between a first position wherein the distal end of the punch rod is proximal to the distal end of the punch tube and a second position wherein the distal end of the punch rod is distal to the distal end of the punch tube, and wherein the method comprises the steps of:

positioning a plant specimen in the gap; and moving the punch tube from its first location to its second location to cut a plug from the plant specimen, and to initiate a subsequent movement of the punch rod from its first position to its second position to remove the cut plant specimen plug from the formed aperture for collection thereof.

18. A method as recited in claim 17 wherein the device further comprises a source of liquid, and a transfer tube having a first end and a second end, wherein the first end is connected in fluid communication with the source of liquid and the second end is positioned to selectively deliver liquid therefrom onto the respective distal ends of the punch tube and the punch rod, and onto the formed aperture, and the method further comprises the step of transferring liquid through the transfer tube to prevent clogging of the device with solid and liquid plant debris.

19. A method as recited in claim 18 wherein the liquid transferring step is automatically accomplished after a set of approximately fifty (50) plugs have been cut.

20. A method as recited in claim 17 wherein the distal end of the punch tube is formed with a pair of diametrically opposed projections.

* * * * *